(12) United States Patent
Rao et al.

(10) Patent No.: US 8,214,225 B2
(45) Date of Patent: Jul. 3, 2012

(54) PATIENT DATA MINING, PRESENTATION, EXPLORATION, AND VERIFICATION

(75) Inventors: R. Bharat Rao, Berwyn, PA (US); Sathyakama Sandilya, Cranbury, NJ (US); Radu Stefan Niculescu, Pittsburgh, PA (US); Arun Kumar Goel, Edison, NJ (US); Brian Berenbach, Edison, NJ (US)

(73) Assignees: Siemens Medical Solutions USA, Inc., Malvern, PA (US); Siemens Corporation, Iselin, NJ (US)

( * ) Notice: Subject to any disclaimer, the term of this patent is extended or adjusted under 35 U.S.C. 154(b) by 1890 days.

(21) Appl. No.: 10/287,075

(22) Filed: Nov. 4, 2002

(65) Prior Publication Data
US 2003/0120514 A1  Jun. 26, 2003

Related U.S. Application Data

(60) Provisional application No. 60/335,542, filed on Nov. 2, 2001.

(51) Int. Cl.
*G06Q 10/00* (2012.01)
*G06Q 50/00* (2012.01)

(52) U.S. Cl. .................................. 705/2; 705/3
(58) Field of Classification Search .................. 705/2–3
See application file for complete search history.

(56) References Cited

U.S. PATENT DOCUMENTS

| | | |
|---|---|---|
| 4,946,679 A | 8/1990 | Thys-Jacobs |
| 5,172,418 A | 12/1992 | Ito et al. |
| 5,307,262 A | 4/1994 | Ertel |
| 5,359,509 A | 10/1994 | Little et al. |
| 5,365,425 A | 11/1994 | Torma et al. |
| 5,508,912 A | 4/1996 | Schneiderman |
| 5,544,044 A | 8/1996 | Leatherman |
| 5,557,514 A | 9/1996 | Seare et al. |
| 5,619,991 A | 4/1997 | Sloane |
| 5,652,842 A | 7/1997 | Siegrist, Jr. et al. |
| 5,657,255 A | 8/1997 | Fink et al. |
| 5,664,109 A * | 9/1997 | Johnson et al. .................. 705/2 |
| 5,669,877 A | 9/1997 | Blomquist |

(Continued)

FOREIGN PATENT DOCUMENTS

DE   198 20 276   11/1999

(Continued)

OTHER PUBLICATIONS

"Machine Learning and Data Mining", Mitchell, Communications of the ACM, Nov. 1999, ACM, USA. Onlinel, vol. 42. No. 11, Nov. 1999, pp. 30-36. retrieved from Internet http://portal.acm.org/ft_gateway.cfm!.

(Continued)

*Primary Examiner* — Sheetal R Rangrej
(74) *Attorney, Agent, or Firm* — Joshua Ryan (57) ABSTRACT

The present invention provides a graphical user interface for presentation, exploration and verification of patient information. In various embodiments, a method is provided for browsing mined patient information. The method includes selecting patient information to view, at least some of the patient information being probabilistic, presenting the selected patient information on a screen, the selected patient information including links to related information. The selected patient information may include elements, factoids, and/or conclusions. The selected patient information may include an element linked to unstructured information. For example, an element linked to a note with highlighted information may be presented. Additionally, the unstructured information may include medical images and waveform information.

30 Claims, 13 Drawing Sheets

U.S. PATENT DOCUMENTS

| | | | |
|---|---|---|---|
| 5,706,441 A | 1/1998 | Lockwood | |
| 5,724,379 A | 3/1998 | Perkins et al. | |
| 5,724,573 A | 3/1998 | Agrawal et al. | |
| 5,737,539 A | 4/1998 | Edelson et al. | |
| 5,738,102 A | 4/1998 | Lemelson | |
| 5,811,437 A | 9/1998 | Singh et al. | |
| 5,832,450 A | 11/1998 | Myers et al. | |
| 5,835,897 A | 11/1998 | Dang | |
| 5,845,253 A | 12/1998 | Rensimer et al. | |
| 5,899,998 A * | 5/1999 | McGauley et al. | 707/104.1 |
| 5,903,889 A | 5/1999 | de la Huerga et al. | 707/3 |
| 5,908,383 A | 6/1999 | Brynjestad | |
| 5,924,073 A | 7/1999 | Tyuluman et al. | |
| 5,924,074 A * | 7/1999 | Evans | 705/3 |
| 5,935,060 A | 8/1999 | Iliff | |
| 5,939,528 A | 8/1999 | Clardy et al. | |
| 5,991,731 A | 11/1999 | Colon et al. | |
| 6,039,688 A | 3/2000 | Douglas et al. | |
| 6,067,466 A | 5/2000 | Selker et al. | |
| 6,076,088 A | 6/2000 | Paik et al. | |
| 6,078,894 A | 6/2000 | Clawson et al. | |
| 6,081,786 A | 6/2000 | Barry et al. | |
| 6,083,693 A | 7/2000 | Nandabalan et al. | |
| 6,108,635 A | 8/2000 | Herren et al. | |
| 6,125,194 A | 9/2000 | Yeh et al. | |
| 6,128,620 A | 10/2000 | Pissanos et al. | |
| 6,139,494 A | 10/2000 | Cairnes | |
| 6,151,581 A | 11/2000 | Kraftson et al. | |
| 6,173,280 B1 | 1/2001 | Ramkumar et al. | |
| 6,196,970 B1 | 3/2001 | Brown | |
| 6,212,519 B1 * | 4/2001 | Segal | 1/1 |
| 6,212,526 B1 | 4/2001 | Chaudhuri et al. | |
| 6,253,186 B1 | 6/2001 | Pendleton, Jr. | |
| 6,259,890 B1 | 7/2001 | Driscoll et al. | |
| 6,266,645 B1 | 7/2001 | Simpson | |
| 6,272,472 B1 | 8/2001 | Danneels et al. | |
| 6,322,502 B1 * | 11/2001 | Schoenberg et al. | 600/300 |
| 6,322,504 B1 | 11/2001 | Kirshner | |
| 6,338,042 B1 | 1/2002 | Paizis | |
| 6,381,576 B1 | 4/2002 | Gilbert | |
| 6,468,210 B1 | 10/2002 | Iliff | |
| 6,478,737 B2 | 11/2002 | Bardy | |
| 6,484,144 B2 | 11/2002 | Martin et al. | |
| 6,523,019 B1 | 2/2003 | Borthwick | |
| 6,529,876 B1 | 3/2003 | Dart | |
| 6,551,243 B2 | 4/2003 | Bocionek et al. | |
| 6,551,266 B1 | 4/2003 | Davis, Jr. | |
| 6,587,829 B1 | 7/2003 | Camarda et al. | |
| 6,611,825 B1 | 8/2003 | Billheimer et al. | |
| 6,611,846 B1 | 8/2003 | Stoodley | |
| 6,641,532 B2 | 11/2003 | Iliff | |
| 6,645,959 B1 | 11/2003 | Bakker-Arkema et al. | |
| 6,678,669 B2 | 1/2004 | Lapointe et al. | |
| 6,754,655 B1 | 6/2004 | Segal | |
| 6,802,810 B2 | 10/2004 | Ciarniello et al. | |
| 6,804,656 B1 | 10/2004 | Rosenfeld et al. | |
| 6,826,536 B1 | 11/2004 | Forman | |
| 6,839,678 B1 | 1/2005 | Schmidt et al. | |
| 6,903,194 B1 | 6/2005 | Sato et al. | |
| 6,915,254 B1 | 7/2005 | Heinze et al. | |
| 6,915,266 B1 | 7/2005 | Saeed et al. | |
| 6,941,271 B1 | 9/2005 | Soong | |
| 6,961,687 B1 | 11/2005 | Myers, Jr. et al. | |
| 6,988,075 B1 * | 1/2006 | Hacker | 705/3 |
| 7,058,658 B2 | 6/2006 | Mentzer | |
| 7,130,457 B2 | 10/2006 | Kaufman et al. | |
| 7,249,006 B2 | 7/2007 | Lombardo et al. | |
| 7,307,543 B2 | 12/2007 | Rosenfeld et al. | |
| 7,353,238 B1 | 4/2008 | Gliklich | |
| 7,630,908 B1 | 12/2009 | Amrien et al. | |
| 2001/0011243 A1 | 8/2001 | Dembo et al. | |
| 2001/0023419 A1 | 9/2001 | LaPointe et al. | |
| 2001/0032195 A1 | 10/2001 | Graichen et al. | |
| 2001/0041991 A1 | 11/2001 | Segal et al. | |
| 2001/0051882 A1 | 12/2001 | Murphy et al. | |
| 2002/0002474 A1 | 1/2002 | Michelson et al. | |
| 2002/0010597 A1 * | 1/2002 | Mayer et al. | 705/2 |
| 2002/0026332 A1 * | 2/2002 | Snowden et al. | 705/3 |
| 2002/0032581 A1 | 3/2002 | Reitberg | |
| 2002/0035316 A1 | 3/2002 | Drazen | |
| 2002/0077853 A1 | 6/2002 | Boru et al. | |
| 2002/0082480 A1 | 6/2002 | Riff et al. | |
| 2002/0087361 A1 | 7/2002 | Benigno et al. | |
| 2002/0099570 A1 | 7/2002 | Knight | |
| 2002/0123905 A1 | 9/2002 | Goodroe et al. | |
| 2002/0138492 A1 | 9/2002 | Kil | |
| 2002/0138524 A1 | 9/2002 | Ingle et al. | |
| 2002/0143577 A1 | 10/2002 | Shiffman et al. | |
| 2002/0165736 A1 | 11/2002 | Tolle et al. | |
| 2002/0173990 A1 | 11/2002 | Marasco | |
| 2002/0177759 A1 | 11/2002 | Schoenberg et al. | |
| 2003/0028401 A1 | 2/2003 | Kaufman et al. | |
| 2003/0046114 A1 | 3/2003 | Davies et al. | |
| 2003/0050794 A1 | 3/2003 | Keck | |
| 2003/0108938 A1 | 6/2003 | Pickar et al. | |
| 2003/0120133 A1 | 6/2003 | Rao et al. | |
| 2003/0120134 A1 | 6/2003 | Rao et al. | |
| 2003/0120458 A1 | 6/2003 | Rao et al. | |
| 2003/0125984 A1 | 7/2003 | Rao et al. | |
| 2003/0125985 A1 | 7/2003 | Rao et al. | |
| 2003/0125988 A1 | 7/2003 | Rao et al. | |
| 2003/0126101 A1 | 7/2003 | Rao et al. | |
| 2003/0130871 A1 | 7/2003 | Rao et al. | |
| 2003/0135391 A1 | 7/2003 | Edmundson et al. | |
| 2003/0208382 A1 | 11/2003 | Westfall | |
| 2004/0067547 A1 | 4/2004 | Harbron et al. | |
| 2004/0078216 A1 | 4/2004 | Togo | |
| 2004/0184644 A1 | 9/2004 | Leichter et al. | |
| 2004/0243586 A1 | 12/2004 | Byers | |
| 2005/0187794 A1 * | 8/2005 | Kimak | 705/3 |
| 2005/0191716 A1 | 9/2005 | Surwit et al. | |
| 2006/0064415 A1 | 3/2006 | Guyon et al. | |
| 2006/0122864 A1 | 6/2006 | Gottesman et al. | |
| 2006/0136259 A1 | 6/2006 | Weiner et al. | |

FOREIGN PATENT DOCUMENTS

| | | |
|---|---|---|
| EP | 0 596 247 A2 | 9/1993 |
| EP | 0 641 863 | 3/1995 |
| EP | 0 917 078 A1 | 10/1997 |
| GB | 2 332 544 A | 6/1999 |
| JP | 11328073 A | 11/1999 |
| WO | WO 98/29790 | 7/1998 |
| WO | 98/39720 | 9/1998 |
| WO | WO 00/51054 | 8/2000 |
| WO | WO 00/69331 | 11/2000 |
| WO | WO 01/66007 | 9/2001 |
| WO | 2001297157 A | 10/2001 |
| WO | WO 01/78005 A2 | 10/2001 |
| WO | 01/82173 A1 | 11/2001 |

OTHER PUBLICATIONS

"Data mining for the Enterprise", Kleissner, System Sciences, 1998, Proceedings of the Thirty-First Hawaii International Conference on Kohala Coast, HI, USA Jan. 6-9, 1998, Los Alamitos, CA, USA. IEEE Comput Soc. US, Jan. 6, 1998, pp. 295-304.

"Improved Diagnostic and Prognostic Assessments Using Health Management Information Fusion". Roemer at el., 20001 IEEE Autotestcon Proceedings, IEEE Systems Readiness Technology Conference, Autotestcon 2001. vol. CONF. 37, Aug. 20, 2001, pp. 365-377.

"Data Mining for Disease Management: Adding Value to Patient Records", Rao at el., Electromedia, Online!, vol. 68, 2000, pp. 63-67. retrieved from the Internet: http://www.med.siemens.com/medroot/en/news/electro/Issues/pdf/onco_2000_e/9.pdf.

"Information Understanding Integrating Data Fusion and Data Mining Processes", Waltz et al, Circuits and Systems. 1998, ISCAS 98, Proceedings of the 1998 IEEE International Symposium on Monterey, CA USA May 31-Jun. 3, 1998, NY, NY, USA, IEEE, May 31, 1998, pp. 553-556.

"A Mutually Beneficial Integration of Data Mining and Information Extraction", Nahm et al., Proceedings AAAI, National Conference on Artificial Intelligence, Jul. 30, 2000, pp. 627-632.

"Using Data Mining to Characterize DNA Mutations by Patient Clinical Features", Evans at el., 1997 AMIA Annual Fall Symposium, Proceedings of 1997 AMIA Annual Fall Symposium the Emergence of Internetable Health Care Systems That Really Work, Nashville, TN, pp. 253-257.

"The Colorectal Cancer Recurrence Support (CARES) System", Ong et al., Artificial Intelligence in Medicine, Nov. 1997, Elsevier, Netherlands, vol. 11, No. 3, pp. 175-188.

"Database System Support for Multidimensional Data Analysis in Environmental Epidemiology", Kamp et al., Database Engineering and Applications Symposium, 1997, Ideas 97, Proceedings, International Montreal, Oue, Canada, Aug. 25-27, 1997, Los Alamitos, CA, USA, IEEE Comput. Soc., US, pp. 180-188.

Mills, "Computer Technology of the Not-too-distant Future", Sep. 1993, Medical Laboratory Observer, vol. 25, No. 9, p. 78.

Duda, "Pattern Classification", 2001, John Wiley & Sons, Inc., p. vii-xx, Chapter 1.

Hudson, "The feasibility of using automated data to assess guideline-concordant care for schizophrenia", Dec. 4, 1999, Journal of Medical Systems, vol. 23, No. 4, pp. 299-307.

PR Newsire, Diabetes Health Management Award Honors Mayor Clinic's Zimmerman, Sep. 25, 2000.

Hudson, "CAATS and compliance", Apr. 1998, The Internal Auditor, vol. 55, No. 2, p. 25.

Hofer, "The Unreliability of Individual Physician "Report Cards" for Assessing the Costs and Quality of Care of a Chronic Disease", Jun. 9, 1999, JAMA, vol. 281, No. 22:2098-2105.

King et al., MEDUS/A: Distributing Database Management for Medical Research, Proceedings of Computer Networks Compcon 82, Sep. 20-23, 1982, pp. 635-642.

Boxwala et al., "Architecture for a Multipurpose Guideline Execution Engine", Proc. AMIA Symp 1999, pp. 701-705.

Guidance for Institutional Review Boards and Clinical Investigators 1998 Update, Sep. 1998, U.S. Food and Drug Administration.

Kassirer, "The Use and Abuse of Practice Profiles", Mar. 3, 1994, The New England Journal of Medicine, vol. 330:634-636.

Chen, "Do "America's Best Hospitals" Perform Better for Acute Myocardial Infarctions?", Jan. 28, 1999, The New England Journal of Medicine, vol. 340, No. 4:286-292.

Dato, et al., The Nation's Current Capacity for the Early Detection of Public Health Threats Including Bioterrorism, Agency for Healthcare Research and Quality, Jun. 8, 2001.

Hanson, et al., Bayesian Classification Theory, Technical Report FIA-90-12-7-01, 1991, pp. 1-10.

Diadoo, Cindy A., An Assessment for the Need of a Bioterrorism Preparedness Plan at Hospital XYZ in Minnesota, The Graduate College, University of Wisconsin-Stout, Dec. 1999, pp. 1-57.

Wagner, et al., Availability and Comparative Value of Data Elements Required for an Effective Bioterrorism Detection System, Nov. 28, 2001, Agency for Healthcare Research and Quality, pp. 1-184.

Bregg, et al., Assessment of Diagnostic Tests When Disease is Subject to Selection Bias, Biometrics, vol. 39, No. 1, Mar. 1983, pp. 207-215.

Grimes, "Structure, Models and Meaning, Is "Unstructured" Data Merely Unmodeled?", Mar. 1, 2005, Intelligent Enterprise. http://www.intelligententerprise.com/showArticle.jhtml?articleID=59301538.

Berkus, "Unstructured Data" as an Oxymoron, Sep. 1, 2005, ITtoolbox Blogs, http://blogs.ittoolbox.com/database/soup/archives/unstructured-data-as-an-oxymoron-5588.

Larsen, "Fast and effective text mining using linear-time document clustering", 1999, ACM Press. Conference on Knowledge Discovery in Data, Proceedings of the fifth ACM SIGKDD International Conference on Knowledge Discovery and Data Mining, pp. 16-22.

Rao, "From Unstructured Data to Actionable Intelligence", IT Pro, Nov./Dec. 2003, pp. 29-35.

* cited by examiner

PATIENT'S ELEMENTS MINER - <0028>
File View Sort Navigate Help

- Summary of Patient 0028
  - All Elements ( 26 elems, 12 categs)
    - AmiEnzymesLevel (1 elems)
    - BGLUT (5 elems)
    - CKMBRI (2 elems)
    - Date of visit (1 elems)
    - DiabetesEnzymes (1 elems)
    - GLU (3 elems)
    - MBCPK (2 elems)
    - STTAbn (3 elems)
    - TCPK (3 elems)
    - TcpkLevel (1 elems)
    - TROPONIN (3 elems)
    - TroponinLevel (1 elems)
  - All Documents
    - Dictations (4 docs, 4 elems, 2 categs)
      - Doc: HEADER 0 (1 elems, 1 categs)
      - Doc: ER 1 (2 elems, 1 categs)
        - STTAbn (2 elems)
      - Doc: Ekg 10 (1 elems, 1 categs)
      - Doc: DS 2 (0 elems, 0 categs)
    - EKG notes
    - All Lab Results
    - Medication
  - All Tests
    - TROPONIN
    - TCPK
    - MBCPK
    - CKMBRI
    - BGLUT
    - GLU
  - Glycemic Control

Showing whole document – ER notes

ER NOTES (ER)
****

ATTENDING PHYSICIAN ADDENDUM:
I evaluated this patient with the Trauma team. This is a Level I trauma who is brought by STAT MedEvac II Air Transport from the scene of a car roll-over.
This is a **AGE<in 60s>-year-old female who was an unrestrained driver involved in a roll-over car crash. Was initially unresponsive, but became responsive to deep sternal rub. Subsequently, during the transport, the patient became more somnolent and required endotracheal intubation just prior to landing. No other history is available, at this time, secondary to the patient being intubated.
Physical examination: The patient arrives intubated, in full C-spine immobilization on a back board, in CID and cervical collar. The patient is responding to some commands and moves her right foot to command on arrival. Vital signs during the primary survey were temperature 36.1, pulse 83, respirations 24 assisted, and blood pressure 190/110. EKG demonstrated a sinus rhythm. The airway was intubated. There were clear breath sounds bilaterally. Normal heart tones. No JVD or tracheal deviation. Symmetrical chest expansion without any crepitus or tenderness. GCS is 8T. The patient does obey commands on arrival. Pupils are 3 mm and briskly reactive bilaterally. TMs are clear bilaterally. Head reveals a laceration of the right forehead area which is approximately 4 cm. Neck reveals no step-offs and there is no facial trauma. Abdomen is soft and nondistended, nontender. Rectal reveals normal tone and guaiac-negative. Pelvis is stable.

- Summary of Patient 0005
  - All Elements (89 elems, 20 categs)
    - AmiEnzymesLevel (1 elems)
    - BGLUT (38 elems)
    - CKMBR (1 elems)
    - Date of visit (1 elems)
    - Diabetes (5 elems)
    - DiabetesDrugs (6 elems)
    - DiabetesEnzymes (1 elems)
    - DiabetesMedication (12 elems)
    - DiabetesRuleFired (3 elems)
    - GLU (5 elems)
    - MBCPK (1 elems)
    - Nephropathy (2 elems)
    - Neuropathy (2 elems)
    - pain (3 elems)
    - Qwave (2 elems)
    - STTAbn (2 elems)
    - TCPK (1 elems)
    - TcpkLevel (1 elems)
    - TROPONIN (1 elems)
    - TroponinLevel (1 elems)
  - All Documents
    - Dictations (4 docs, 23 elems, 8 categs)
      - Doc: HEADER 0 (1 elems, 1 categs)
      - Doc: HP 1 (14 elems, 6 categs)
        - Diabetes (3 elems)
        - DiabetesDrugs (4 elems)
        - Nephropathy (2 elems)
        - Neuropathy (2 elems)
        - pain (1 elems)
        - Qwave (2 elems)
      - Doc: ekg 10 (1 elems, 1 categs)
      - Doc: HP 2 (7 elems, 4 categs)
    - EKG notes
    - All Lab Results
    - Medication
  - All Tests
    - TROPONIN
    - TCPK
    - MBCPK
    - CKMBRI
    - BGLUT
    - GLU
  - Glycemic Control All Lab Results – from structured data source

```
5,5 10/14/00 06:09 BGLUT 91
5,5 10/13/00 21:26 BGLUT 129
5,5 10/13/00 16:22 BGLUT 132
5,5 10/13/00 11:05 BGLUT 158
5,5 10/13/00 04:32 BGLUT 170
5,5 10/12/00 21:14 BGLUT 158
5,5 10/12/00 16:10 BGLUT 105
5,5 10/12/00 11:24 BGLUT 86
5,5 10/12/00 05:01 BGLUT 86
5,5 10/12/00 04:00 GLU 69
5,5 10/11/00 20:52 BGLUT 103
5,5 10/11/00 17:20 BGLUT 160
5,5 10/11/00 12:16 BGLUT 92
5,5 10/11/00 04:20 BGLUT 97
5,5 10/10/00 15:16 BGLUT 125
5,5 10/10/00 11:28 BGLUT 153
5,5 10/10/00 05:54 BGLUT 146
5,5 10/09/00 21:25 BGLUT 122
5,5 10/09/00 16:26 BGLUT 107
5,5 10/09/00 10:57 BGLUT 128
5,5 10/09/00 04:09 BGLUT 98
5,5 10/09/00 04:01 GLU 83
5,5 10/08/00 21:35 BGLUT 96
5,5 10/08/00 16:57 BGLUT 127
5,5 10/08/00 06:39 BGLUT 96
5,5 10/07/00 22:35 BGLUT 96
5,5 10/07/00 14:54 GLU 85
5,5 10/07/00 12:42 BGLUT 107
5,5 10/07/00 06:52 BGLUT 92
5,5 10/07/00 00:43 BGLUT 87
5,5 10/06/00 23:15 BGLUT 74
5,5 10/06/00 15:49 BGLUT 155
```

Summary of Patient 0005
- All Elements ( 89 elems, 20 categs)
  - AmlEnzymesLevel (1 elems)
  - BGLUT (38 elems)
  - CKMBRI (1 elems)
  - Date of visit (1 elems)
  - Diabetes (5 elems)
  - DiabetesDrugs (6 elems)
  - DiabetesEnzymes (1 elems)
  - DiabetesMedication (12 elems)
  - DiabetesRuleFired (3 elems)
  - GLU (5 elems)
  - MBCPK (1 elems)
  - Nephropathy (2 elems)
  - Neuropathy (2 elems)
  - pain (3 elems)
  - Qwave (2 elems)
  - STTAbn (2 elems)
  - TCPK (1 elems)
  - TcpkLevel (1 elems)
  - TROPONIN (1 elems)
  - TroponinLevel (1 elems)
- All Documents
  - Dictations (4 docs, 23 elems, 8 categs)
  - EKG notes
  - All Lab Results
  - Medication
- All Tests
  - TROPONIN
  - TCPK
  - MBCPK
  - CKMBRI
  - BGLUT
  - GLU
- Glycemic Control patient id = 0005

Date of event: Tue Oct 03 17:30:00 EDT 2000

BGLUT tests over all time span: 38
Average BGLUT over all time span: 127.47369
Median BGLUT over all time span: 127.5

GLU tests over all time span: 5
Average GLU over all time span: 101.4
Median GLU over all time span: 85.0

BGLUT tests within 24 hrs of event: 0
Average BGLUT within 24 hrs of the event: 0.0
Median BGLUT within 24 hrs of the event: 0.0

GLU tests within 24 hrs of the event: 1
Average GLU within 24 hrs of the event: 147.0
Median GLU within 24 hrs of the event: 147.0

Percentage of glucose values < 200 over all time span: 100.0%
Percentage of glucose values < 200 within 24 hrs of the event: 100.0%

Overall PEGC quality: Excellent
Within 24 hrs PEGC quality: Excellent

PATIENT DATA MINING, PRESENTATION, EXPLORATION, AND VERIFICATION

CROSS REFERENCE TO RELATED APPLICATIONS

This application claims the benefit of U.S. Provisional Application Serial No. 60/335,542, filed on Nov. 2, 2001, which is incorporated by reference herein in its entirety.

FIELD OF THE INVENTION

The present invention relates to organization and review of data, and, more particularly to a graphical user interface for presentation, exploration and verification of patient information.

BACKGROUND OF THE INVENTION

The information environment faced by physicians has undergone significant changes. There is much more information available, in more formats than ever before, competing for the limited time of physicians. Although the information age is slowly transforming this landscape, it has not yet delivered tools that can alleviate the information overload faced by physicians.

Currently, many health care organizations have started to migrate toward environments where most aspects of patient care management are automated. However, health care organizations with such information management systems have tended to maintain information in a myriad of unstructured and structured data sources. It may still be necessary to access numerous different data sources, each with its own peculiar format.

In view of the above, it would be desirable and highly advantageous to provide new graphical tools for presentation, exploration and verification of patient information.

SUMMARY OF THE INVENTION

The present invention provides a graphical user interface for presentation, exploration and verification of patient information.

In various embodiments of the present invention, a method is provided for browsing mined patient information. The method includes selecting patient information to view, at least some of the patient information being probabilistic, presenting the selected patient information on a screen, the selected patient information including links to related information. The selected patient information may include raw information extracted from various data sources for the patient (hereinafter referred to as 'elements') or conclusions drawn therefrom. This information may be derived from various data sources.

The selected patient information may include an element linked to unstructured information. For example, an element linked to a note with highlighted information may be presented. The highlighted information may refer to information used to derive the element. Additionally, the unstructured information may include medical images and waveform information.

The selected patient information may also be derived from structured data sources, such as a database table.

The selected patient information may include a document with links to elements associated with the document.

The selected patient information may include patient summary information.

The patient information presented to a particular user may depend on the identity or role of the user. For instance, a physician may be interested only in a high-level view of the disease (at least initially) and be presented with the most relevant conclusions drawn from the entire patient record.

Another option is to display all the patient information (every element and derived conclusion) but to sort this list in order of decreasing relevance to the disease.

These and other aspects, features and advantages of the present invention will become apparent from the following detailed description of preferred embodiments, which is to be read in connection with the accompanying drawings.

BRIEF DESCRIPTION OF THE DRAWINGS

FIGS. 5 and 6 show exemplary verification screens;

FIGS. 7 and 8 show exemplary exploration screens;

FIGS. 9 and 10 show exemplary results of extraction from a structured data source.

DESCRIPTION OF PREFERRED EMBODIMENTS

Figure 1:
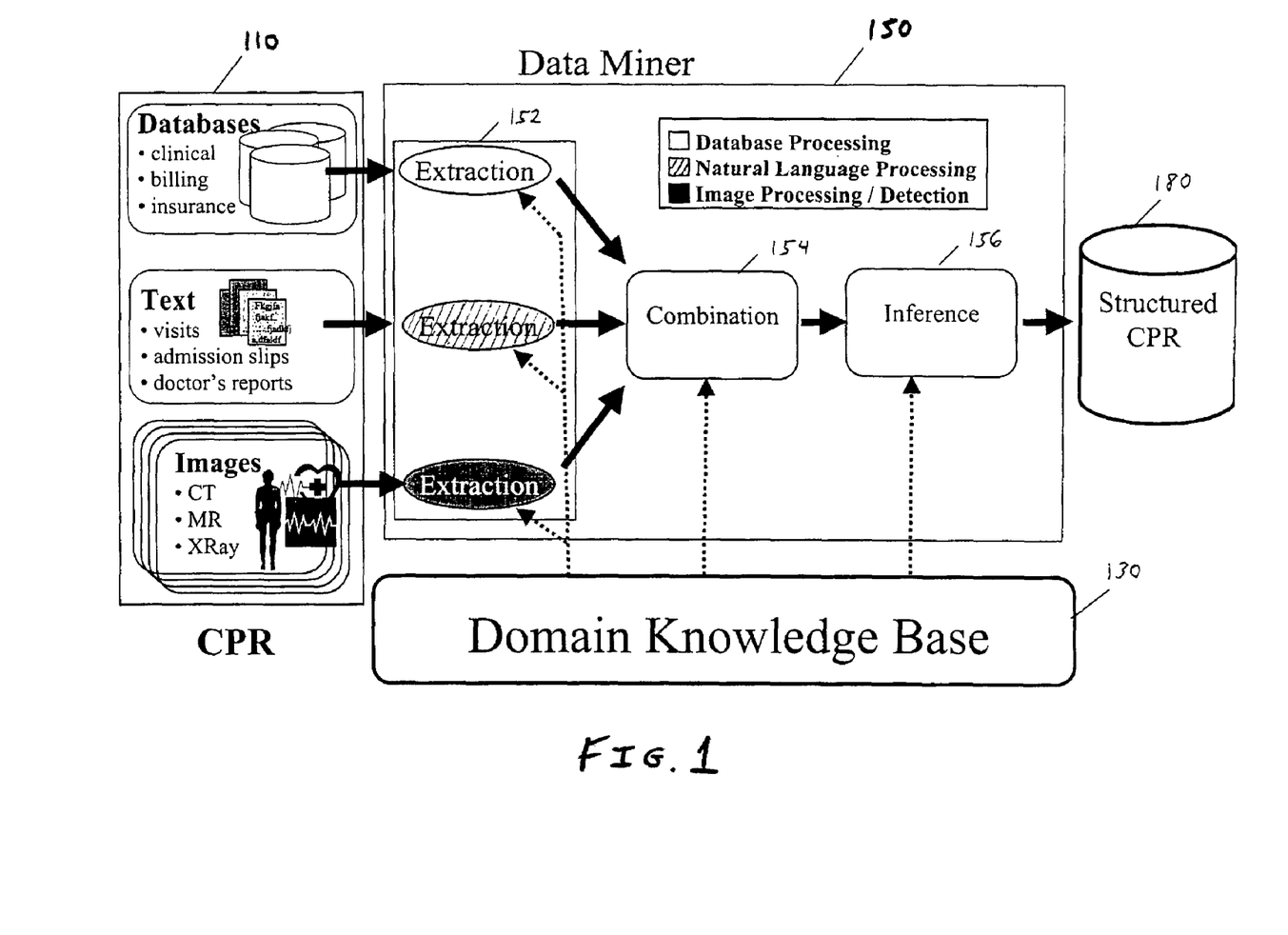
FIG. 1 shows an exemplary data mining framework for mining structured clinical information.

FIG. 1 illustrates an exemplary data mining framework as disclosed in "Patient Data Mining," by Rao et al., copending U.S. patent application Ser. No. 10/287,055, published as 2003-012045, filed herewith, which is incorporated by reference herein in its entirety.

Detailed knowledge regarding the domain of interest, such as, for example, a disease of interest is used. This domain knowledge base can come in two forms. It can be encoded as an input to the system, or as programs that produce information that can be understood by the system. The part of the domain knowledge base that is input to the present form of the system may also be learned from data.

Domain-specific knowledge for mining the data sources may include institution-specific domain knowledge. For example, this may include information about the data available at a particular hospital, document structures at a hospital, policies of a hospital, guidelines of a hospital, and any variations of a hospital.

The domain-specific knowledge may also include disease-specific domain knowledge. For example, the disease-specific domain knowledge may include various factors that influence risk of a disease, disease progression information, complications information, outcomes and variables related to a disease, measurements related to a disease, and policies and guidelines established by medical bodies.

An extraction component takes information from a computerized patient record (CPR) to produce probabilistic assertions (elements) about the patient that are relevant to an instant in time or time period. This process is carried out with the guidance of the domain knowledge that is contained in the domain knowledge base. The domain knowledge required for extraction is generally specific to each source.

Extraction from a text source may be carried out by phrase spotting, which requires a list of rules that specify the phrases of interest and the inferences that can be drawn therefrom. For example, if there is a statement in a doctor's note with the words "There is evidence of metastatic cancer in the liver,"

then, in order to infer from this sentence that the patient has cancer, a rule is needed that directs the system to look for the phrase "metastatic cancer," and, if it is found, to assert that the patient has cancer with a high degree of confidence (which, in the present embodiment, translates to generate an element with name "Cancer", value "True" and confidence 0.9).

The data sources include structured and unstructured information. Structured information may be converted into standardized units, where appropriate. Unstructured information may include ASCII text strings, image information in DICOM (Digital Imaging and Communication in Medicine) format, and text documents partitioned based on domain knowledge. Information that is likely to be incorrect or missing may be noted, so that action may be taken. For example, the mined information may include corrected information, including corrected ICD-9 diagnosis codes.

Extraction from a database source may be carried out by querying a table in the source, in which case, the domain knowledge needs to encode what information is present in which fields in the database. On the other hand, the extraction process may involve computing a complicated function of the information contained in the database, in which case, the domain knowledge may be provided in the form of a program that performs this computation whose output may be fed to the rest of the system.

Extraction from images, waveforms, etc., may be carried out by image processing or feature extraction programs that are provided to the system.

Combination includes the process of producing a unified view of each variable at a given point in time from potentially conflicting assertions from the same/different sources. In various embodiments of the present invention, this is performed using domain knowledge regarding the statistics of the variables represented by the elements ("prior probabilities").

Inference is the process of taking all the factoids that are available about a patient and producing a composite view of the patient's progress through disease states, treatment protocols, laboratory tests, etc. Essentially, a patient's current state can be influenced by a previous state and any new composite observations.

As illustrates in FIG. 1, an exemplary data mining framework for mining high-quality structured clinical information includes a data miner 150 that mines information from a computerized patient record (CPR) 110 using domain-specific knowledge contained in a knowledge base (130). The data miner 150 includes components for extracting information from the CPR 152, combining all available evidence in a principled fashion over time 154, and drawing inferences from this combination process 156. The mined information may be stored in a structured CPR 180.

The extraction component 152 deals with gleaning small pieces of information from each data source regarding a patient, which are represented as probabilistic assertions about the patient at a particular time. These probabilistic assertions are called elements. The combination component 154 combines all the elements that refer to the same variable at the same time period to form one unified probabilistic assertion regarding that variable. These unified probabilistic assertions are called factoids. The inference component 156 deals with the combination of these factoids, at the same point in time and/or at different points in time, to produce a coherent and concise picture of the progression of the patient's state over time. This progression of the patient's state is called a state sequence.

Figure 2:
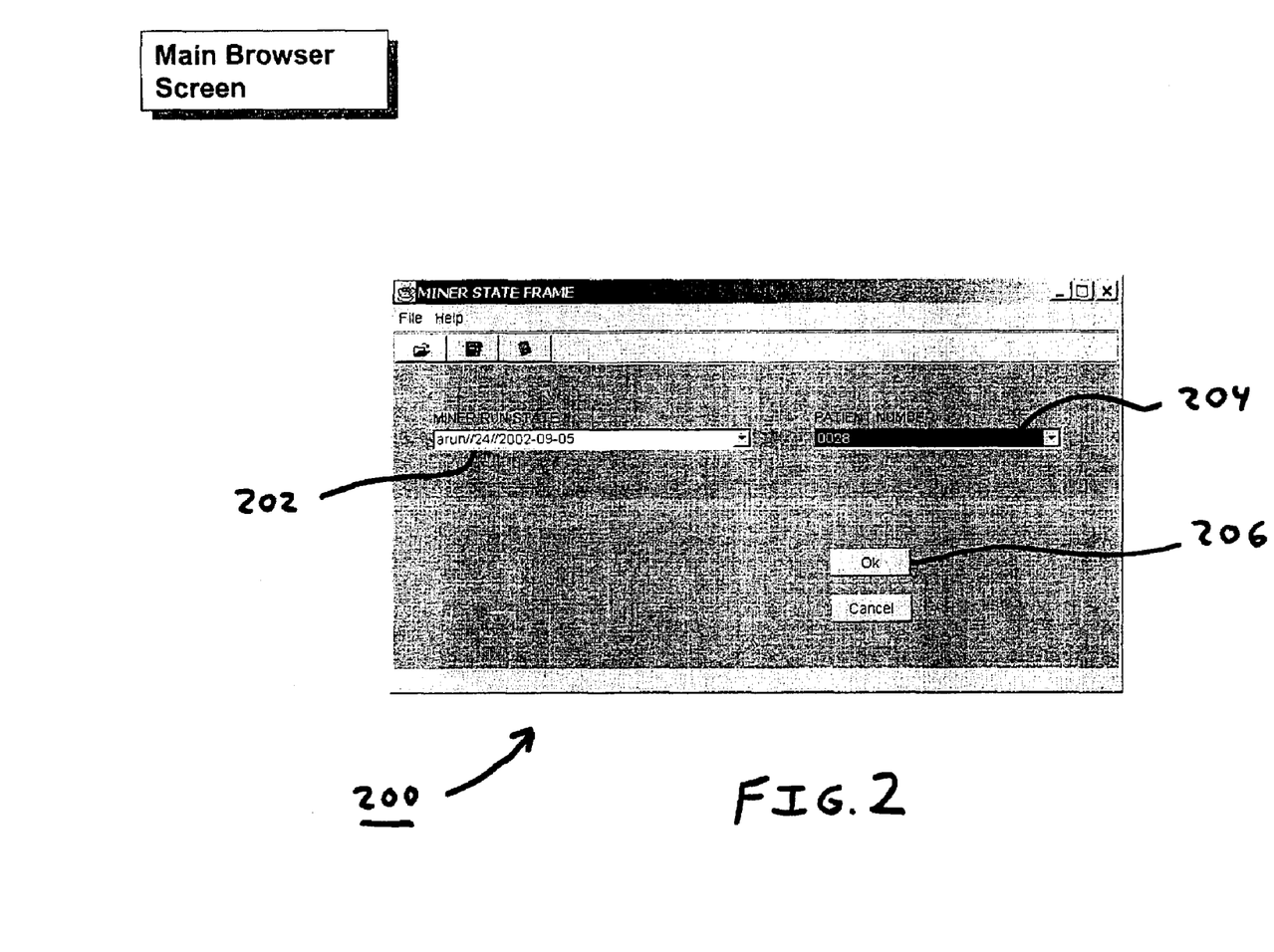
FIG. 2 shows an exemplary main browser screen.

FIG. 2 illustrates an exemplary main browser screen 200 for browsing mined patient information. The exemplary main browser screen 200 includes a run state selector 202, a patient selector 204, and an enter button 206.

In operation, a user interacting with the main browser screen 200 enters a patient identifier using the patient selector 204 and a data mining run state using the run state selector 202. The user then clicks on the enter button 206 to cause the selected patient identifier and run state to be input.

The data mining run state can include a particular run cycle (e.g., run date, time) that patient medical records were mined. When information is retrieved, it can include only information current as of that point.

Figure 3:
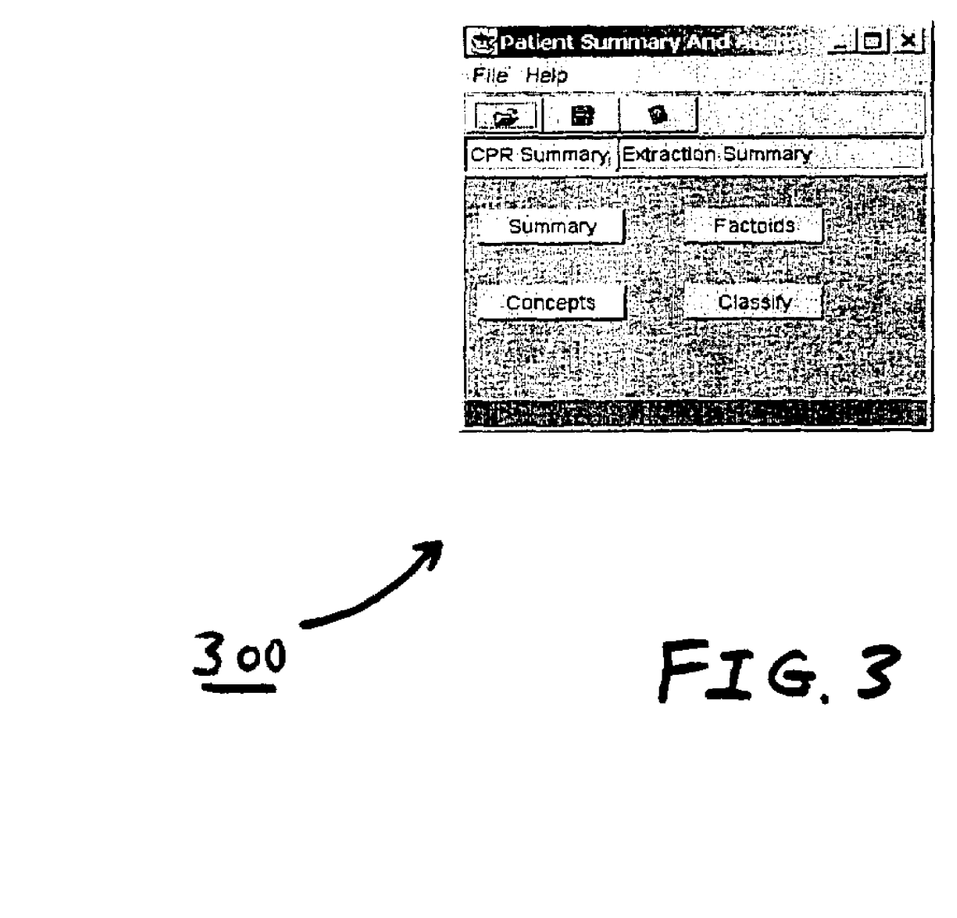
FIG. 3 shows an exemplary options screen.
Figure 4:
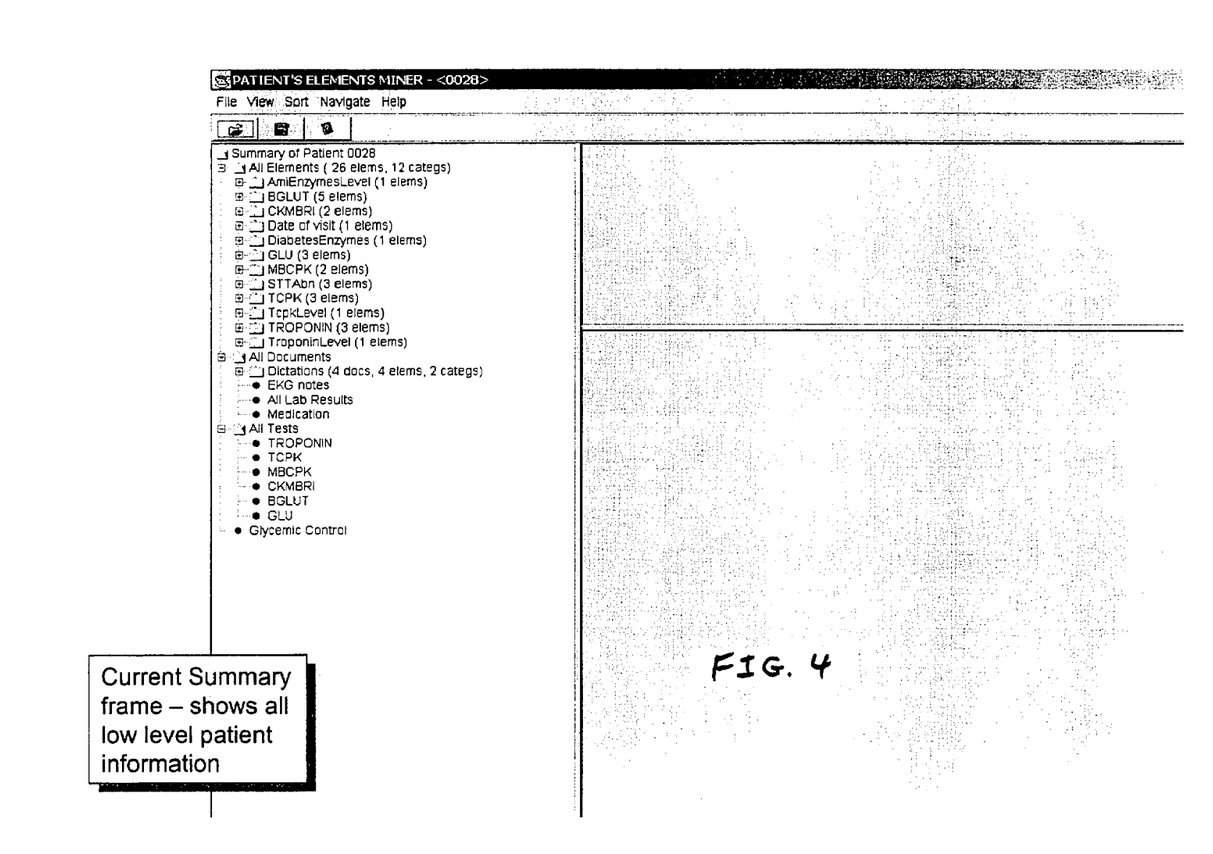
FIG. 4 shows an exemplary summary frame screen.

Referring to FIG. 3, an exemplary options screen 300 is illustrated. The options screen 300 may include a plurality of input buttons, each input button for displaying a level of information. For example, the user may click on an input button to select summary information. FIG. 4 illustrates the result of selecting summary information from the options screen 300. As shown in FIG. 4, a summary of a particular patient information is presented. This summary includes all elements, documents, and tests for the patient relating to glycemic control, which is the view of the patient record presented to the particular user.

Advantageously, the patient information presented to a particular user may depend on the identity or role of the user. For example, a cardiologist may be presented with a different view of the data than an oncologist. Similarly, a physician may be presented with information different from that of a nurse or administrative employee. By presenting different views of the patient information, the user can more effectively make use of information that he or she is interested in.

Another option is to display all the patient information (every element and derived conclusion) but to sort this list in order of decreasing relevance to the disease. For instance, one patient's most relevant item may be his abnormal test results, while another patient whose test results are normal may have his family history of cancer be the most relevant item.

Figure 5:
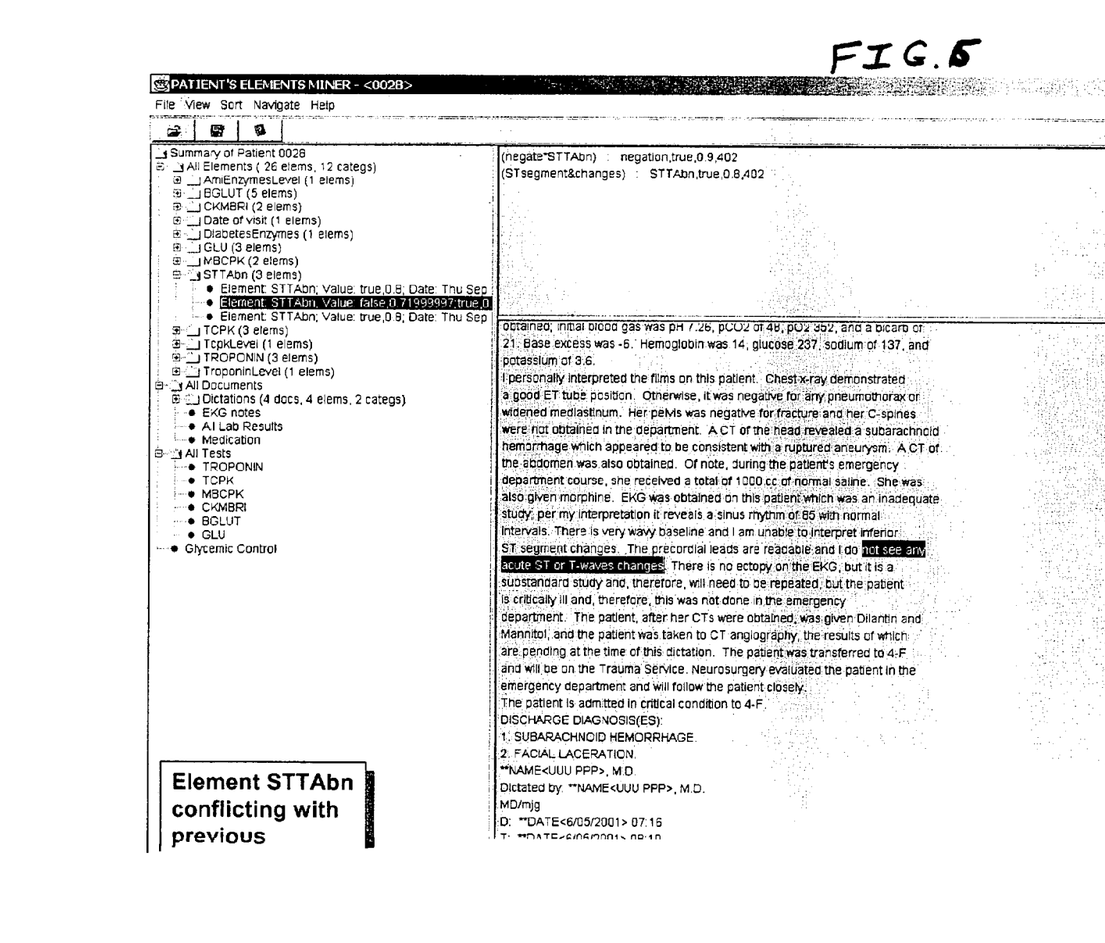

Referring to FIG. 5, an exemplary verification screen is illustrated. This screen allows a user to drill down an element to its underlying source. In this case, the element "STTAbn; Value: true, 0.8" has been selected, causing a physician note to be displayed in the right-hand portion of the screen. The highlighted portion of the physician note indicates the data from which the element was derived. In this case, it was concluded that there is an 80% probability that the patient's ECG showed ST-T wave abnormalities. FIG. 6 illustrates drilling down of another element, "STTabn; Value: false, 0.7", that contradicts the element shown in FIG. 5. In this case, it was concluded that there is an 70% probability that the patient's ECG showed ST-T wave abnormalities. A user may use the verification screen to verify the conclusions inferred from the underlying data sources.

Although FIGS. 5 and 6 show that the underlying data sources are physician notes, it should be appreciated that the data sources could take other forms. For example, the elements may be derived from (and linked to) medical images, waveforms, and structured information (e.g., information contained in a database).

Figure 8:
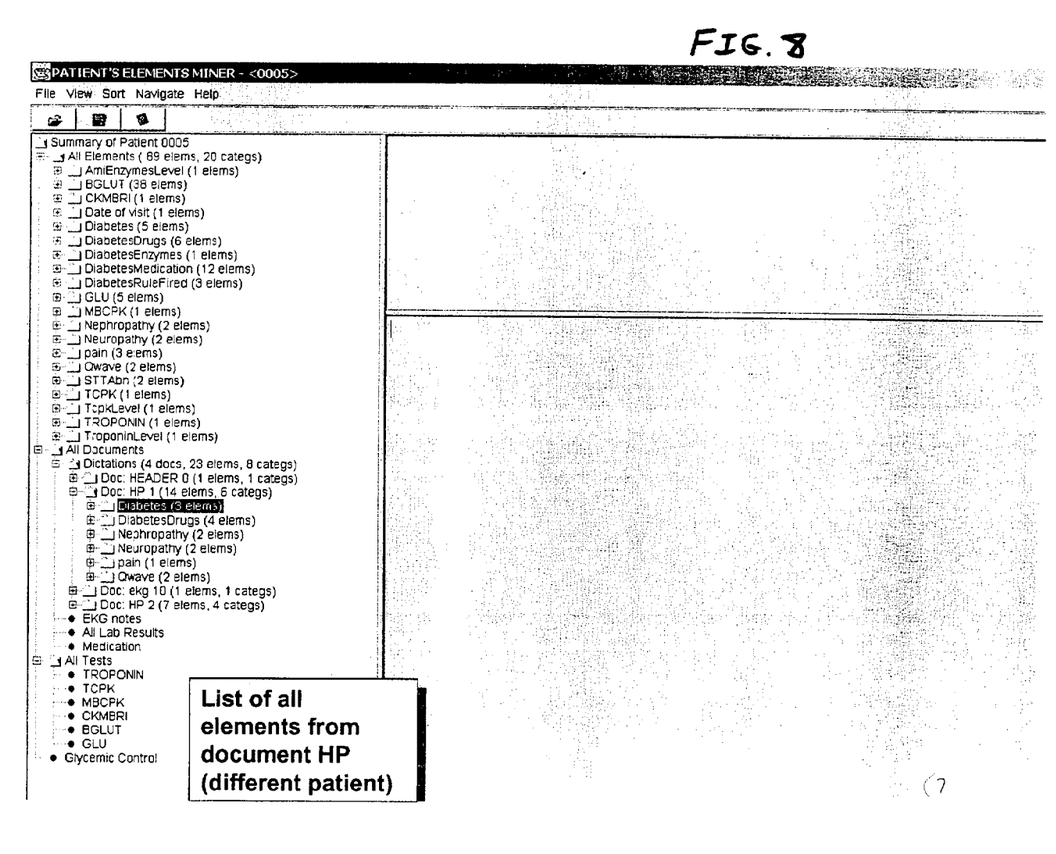

Referring to FIG. 7, documents may be displayed to the user. In this case, the user selected a physician note written by Emergency Room (ER) personnel. Two separate elements were derived from information contained in this document. FIG. 8 shows another document displayed on the exploration screen. As illustrated, this document includes fourteen elements in six categories.

Figure 10:
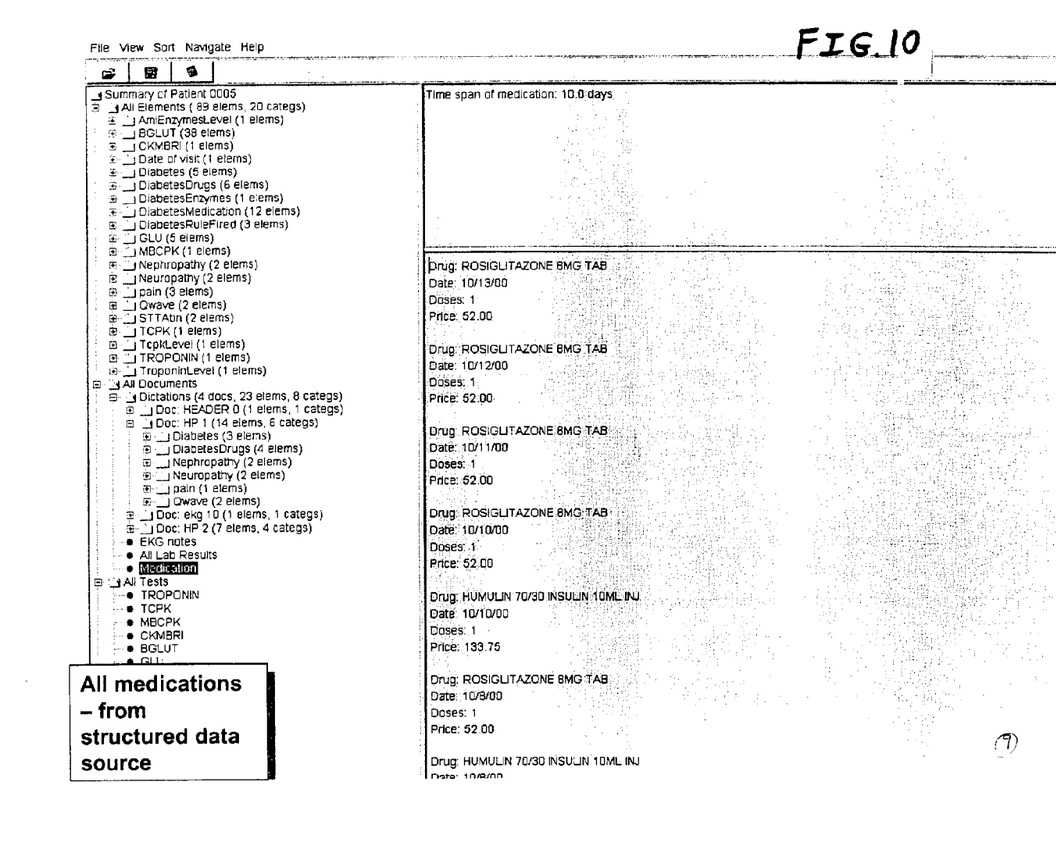

FIGS. 9 and 10 illustrate patient information extracted from structured data sources. In particular, FIG. 9 shows lab results for a particular patient. As depicted, the lab results include a date, time, test name, and measurement value. FIG. 10 shows various medications administered to the patient. This information includes a drug name, date, dosage, and price information. The information obtained from structured data sources may have been converted into standardized units, where appropriate.

Figure 11:
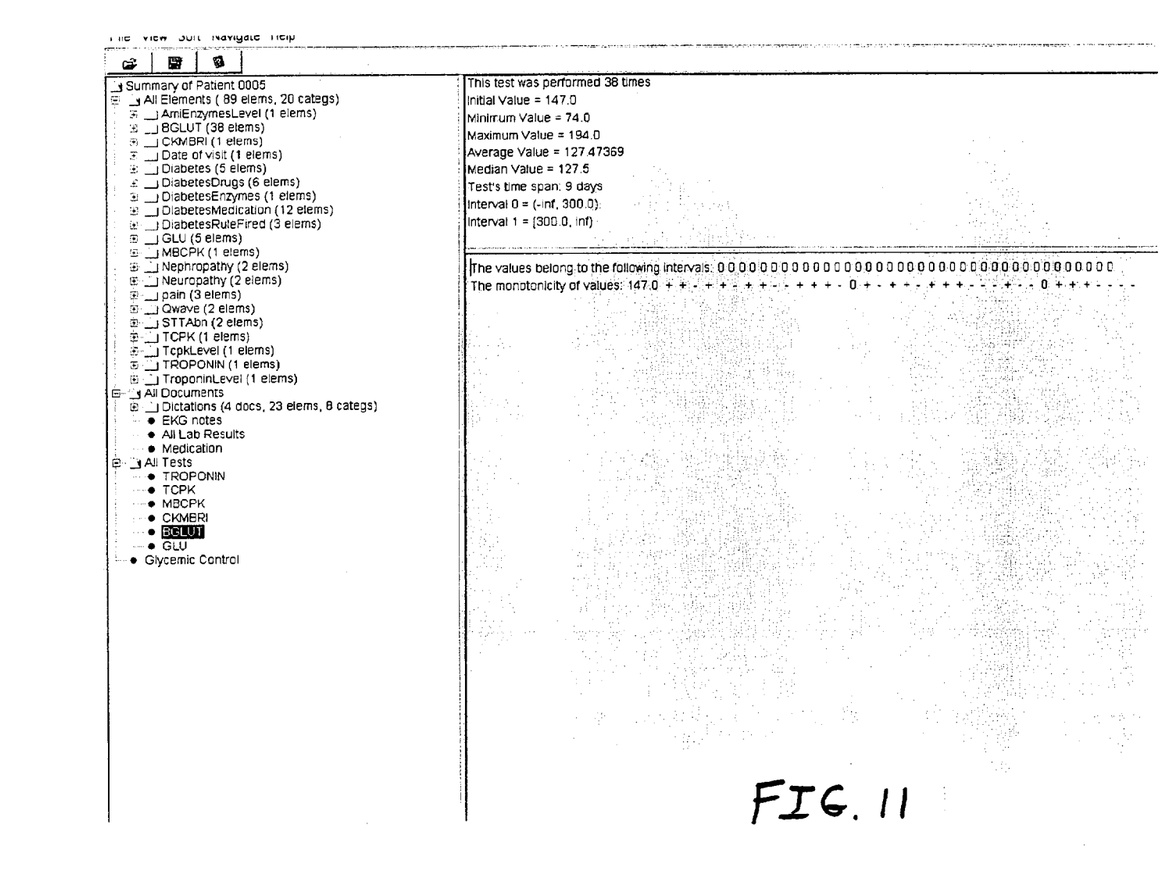
FIGS. 11 to 13 show exemplary presentation of patient summary information.
Figure 12:
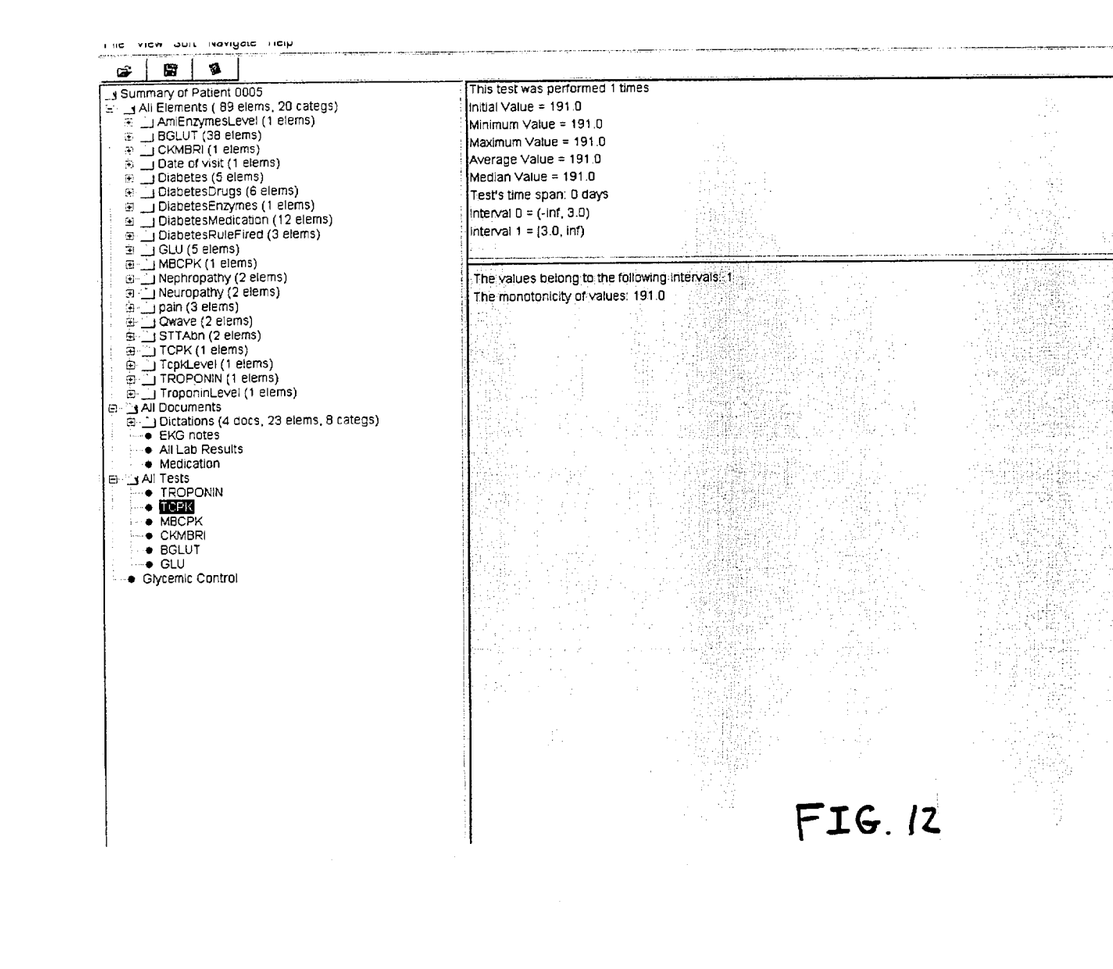
Figure 13:
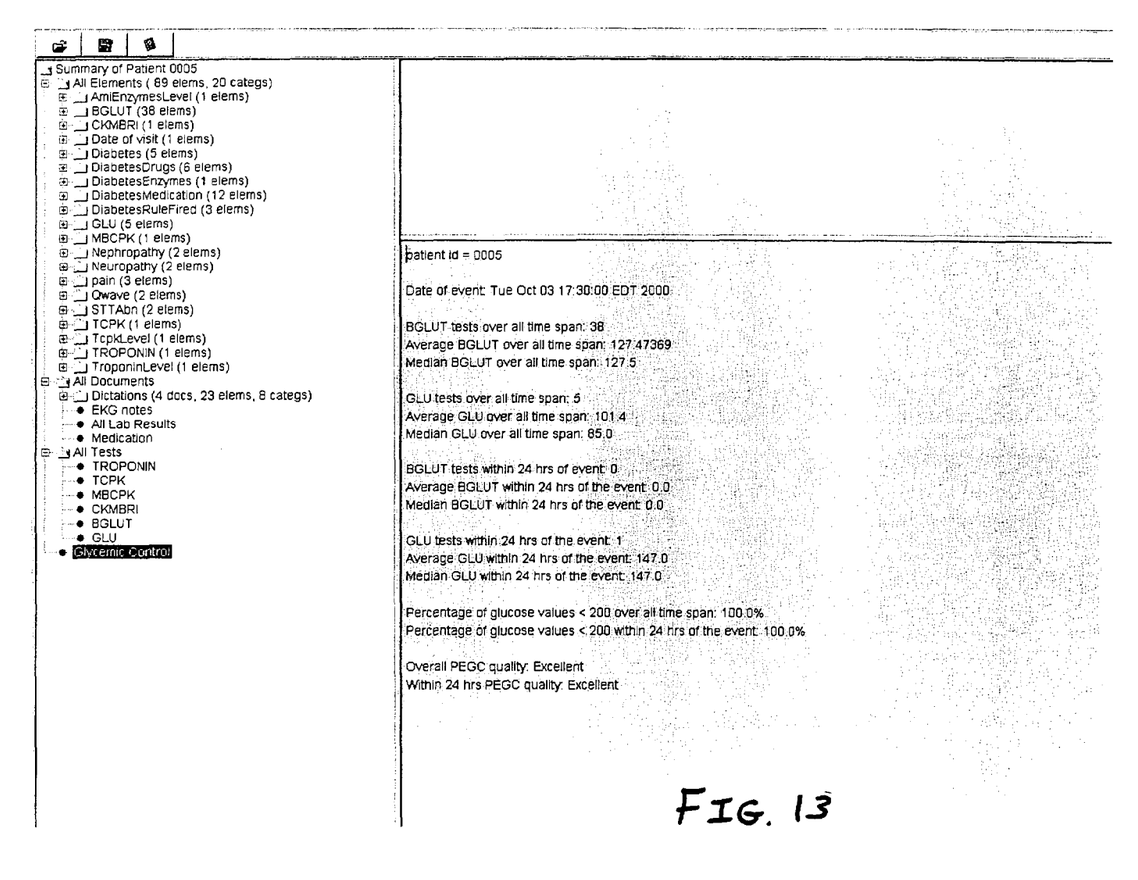

FIGS. 11 to 13 illustrate exemplary patient summary screens. FIG. 11 shows summary results for 'BGLUT' (blood glucose level). As shown, various summary information is presented to the user. Likewise, FIG. 12 shows summary results for "TCPL". As shown in FIG. 13, patient summary information related to various facets of glycemic control is presented.

While the exemplary screens use several selection menus and buttons, it should be appreciated that the selection of various parameters such as the patient identifier, miner run state, documents, elements, categories, etc., can be accommodated using a variety of devices, such as a number of graphical user interface selection widgets, check boxes, buttons, list boxes, pop-up or drop-down marks, text entry boxes and the like, or any known or later developed interfaces that an operator can access. It should be appreciated that the various exemplary screens illustrated herein can also, or alternatively, include any device capable of presentation, exploration, and verification of mined patient information.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for browsing patient information, comprising the steps of:
    mining, by a processor, for patient information, the mining extracting values for respective variables as at least some of the patient information, each of the variables assigned one value, each of the values for each of the multiple variables being derived from multiple pieces extracted from a data source, each of the pieces referring to a same variable being assigned first probabilities indicating likelihoods of the respective variables being the corresponding values, at least one of the first probabilities being less than 100%, each of the values determined with a unified probability determined by combination of the first probabilities from multiple of the pieces referring to the same variable such that the multiple variables are assigned respective values and respective unified probabilities, the pieces and values representing a patient at a particular time;
    selecting at least one of the variables to view the patient information related to the selected one of the variables, the selected patient information related to the selected one of the variables including a subset portion of the data source, the subset portion including the piece extracted for the value of the selected one of the variables and additional information associated with the piece from the data source and not including other information from the data source for the patient, the piece included in the subset portion associated with the first probability used to determine the unified probability of the value for the selected one of the variables;
    presenting the selected patient information on a screen.

2. The method of claim 1, wherein the selected patient information includes one or more of raw information extracted from the data source for the patient and conclusions drawn there from.

3. The method of claim 1, wherein the one of the values is derived from the piece extracted for the one of the values from unstructured data of the data source.

4. The method of claim 1, wherein the selected patient information includes an element linked to unstructured information, the unstructured information including the subset portion.

5. The method of claim 1, wherein the selected patient information includes an element linked to a note with highlighted information.

6. The method of claim 4, wherein the highlighted information refers to information used to derive the element.

7. The method of claim 3, wherein the unstructured information includes one of free text, medical image information, and waveform information.

8. The method of claim 1, wherein the one of the values is inferred from pieces from structured data sources.

9. The method of claim 8, wherein the structured data source includes a database.

10. The method of claim 1, wherein the selected patient information is a document;
    further comprising providing a link to related information associated with the selected patient information, the links to related information referring to the pieces from the document.

11. The method of claim 1, wherein the selected patient information includes summary information.

12. The method of claim 1, wherein selectable patient information is presented based on a view.

13. The method of claim 12, wherein the view is based on a user identifier, a role, or a combination thereof.

14. The method of claim 12, wherein the selected patient information includes summary information.

15. The method of claim 12, wherein the selected patient information is sorted based upon relevance to a disease, a user, or a combination thereof.

16. A program storage device readable by a machine, tangibly embodying a program of instructions executable on the machine to perform method steps for browsing mined patient information, the method steps comprising:
    selecting at least one of multiple variables, the selecting indicating the patient information to view as a subset of the mined patient information, at least some of the mined patient information used to derive a value for the selected one of the variables, the value extracted from a piece of a data source and having a first probability indicating a likelihood of the variable being the value, the first probability determined from a second probability of the piece indicating a likelihood of the variable being the value;
    presenting the selected patient information on a screen, the selected patient information including a portion of the data source, the portion including the piece for the value and additional information associated with the piece from the data source, the piece included in the portion having the second probability used to determine the first probability for the value.

17. The program storage device of claim 16 wherein the step of presenting comprises presenting the selected patient information with a link to related information, the related information comprising the data source.

18. The method of claim 1 wherein the selected patient information includes links to the data source.

19. The method of claim 1 wherein presenting the selected patient information comprises displaying a list of information as a function of relevance to a disease.

20. The method of claim 1 wherein presenting the selected patient information comprises presenting corrected information relative to the patient information.

21. The method of claim 1 wherein mining comprises mining as a function of domain-specific knowledge;
further comprising:
presenting on the screen a list of the values indicative of the domain-specific knowledge.

22. The method of claim 1 wherein presenting comprises presenting an inferred conclusion.

23. The method of claim 1 wherein selecting the patient information comprises selecting at least one of the values from a medical image.

24. The method of claim 1 wherein presenting comprises presenting to a physician.

25. The method of claim 1 wherein presenting comprises presenting to a nurse.

26. The method of claim 1 wherein presenting comprises presenting to an administrative employee.

27. A system for browsing mined patient information, the system comprising:
a data miner configured to mine patient information, the mining extracting values for multiple variables as at least some of the patient information, each of the values being derived from multiple pieces extracted from a data source, the pieces and values representing a patient at a particular time, the pieces assigned first probabilities indicating likelihoods of the variables being the corresponding values, each of the values determined with unified probabilities, each of the unified probabilities being determined by combination of the first probabilities from multiple of the pieces referring to the same variable;
a user input for selecting at least one of the variables for viewing the patient information supporting the value for the selected one of the variables the patient information including a subset portion of the data source, the subset portion including the piece extracted for the one of the values of one of the variables and additional information associated with the piece from the data source, the piece included in the subset portion having the first probability used to determine the unified probability for the value of the selected one of the variables; and
a screen operable to present the patient information.

28. The method of claim 1 wherein mining comprises inferring a state of the variable from a combination of data corresponding to different pieces, the state comprising one of the values;
further comprising storing the state as patient information a structured database;
wherein selecting comprises selecting the variable from the structured database where a corresponding probability is associated with the inferring.

29. The method of claim 1 wherein selecting comprises verifying contradictory data.

30. A method for browsing patient information, the method comprising:
mining for patient information from data in data sources of a computerized patient record, the patient information represented by a probability of a variable having a value for each of a plurality of pieces of the patient information, a final value of the variable determined by combining the probabilities of the pieces of the patient information for the variable, the mining including determining final values for respective multiple variables for a patient;
presenting the patient information on a screen;
receiving user selection of the variable; and
displaying, on the screen, the data associated with the selected variable and supporting the probability, the data supporting the probability including the pieces, one of the pieces being from of a document in one of the data sources, and the data also including a context of the piece and not including other information from the data source for the piece.

* * * * *